US005531519A

United States Patent [19]
Earle

[11] Patent Number: 5,531,519
[45] Date of Patent: Jul. 2, 1996

[54] AUTOMATED BONE CEMENT MIXING APPARATUS

[76] Inventor: Michael L. Earle, 279 Old Ranch Rd., Sierra Madre, Calif. 91024

[21] Appl. No.: 480,924

[22] Filed: Jun. 7, 1995

Related U.S. Application Data

[62] Division of Ser. No. 88,216, Jul. 6, 1993, abandoned.

[51] Int. Cl.$^6$ .................................................. B01F 13/06
[52] U.S. Cl. ...................... 366/139; 366/150.1; 366/191; 366/279
[58] Field of Search .............................. 366/139, 75, 184, 366/279, 169.1, 169.2, 150.1, 191, 348, 349; 99/348; 604/82; 606/92–94; 494/16

[56] References Cited

U.S. PATENT DOCUMENTS

| | | | |
|---|---|---|---|
| 3,366,369 | 1/1968 | Ravasi | 366/139 |
| 3,640,510 | 2/1972 | Lea. | |
| 4,577,973 | 3/1986 | Occelli | 366/139 |
| 4,711,582 | 12/1987 | Kennedy | 366/279 |
| 4,721,390 | 1/1988 | Lidgren | 366/139 |
| 4,854,716 | 8/1989 | Ziemann et al. | 366/139 |
| 4,871,261 | 10/1989 | Randklev | 366/139 |
| 5,143,585 | 9/1992 | Ichikawa et al. | 203/2 |
| 5,145,250 | 9/1992 | Planck | 366/8 |

Primary Examiner—Robert W. Jenkins
Attorney, Agent, or Firm—Christie, Parker & Hale

[57] ABSTRACT

A motorized mixer for mixing bone cement for use in attachment of prosthetics and method for using the mixer. The mixer comprises a mixing chamber, a liner in the mixing chamber, an impeller within the liner, a motor for driving the impeller and programmable means for regulating the operations of the motor.

6 Claims, 12 Drawing Sheets

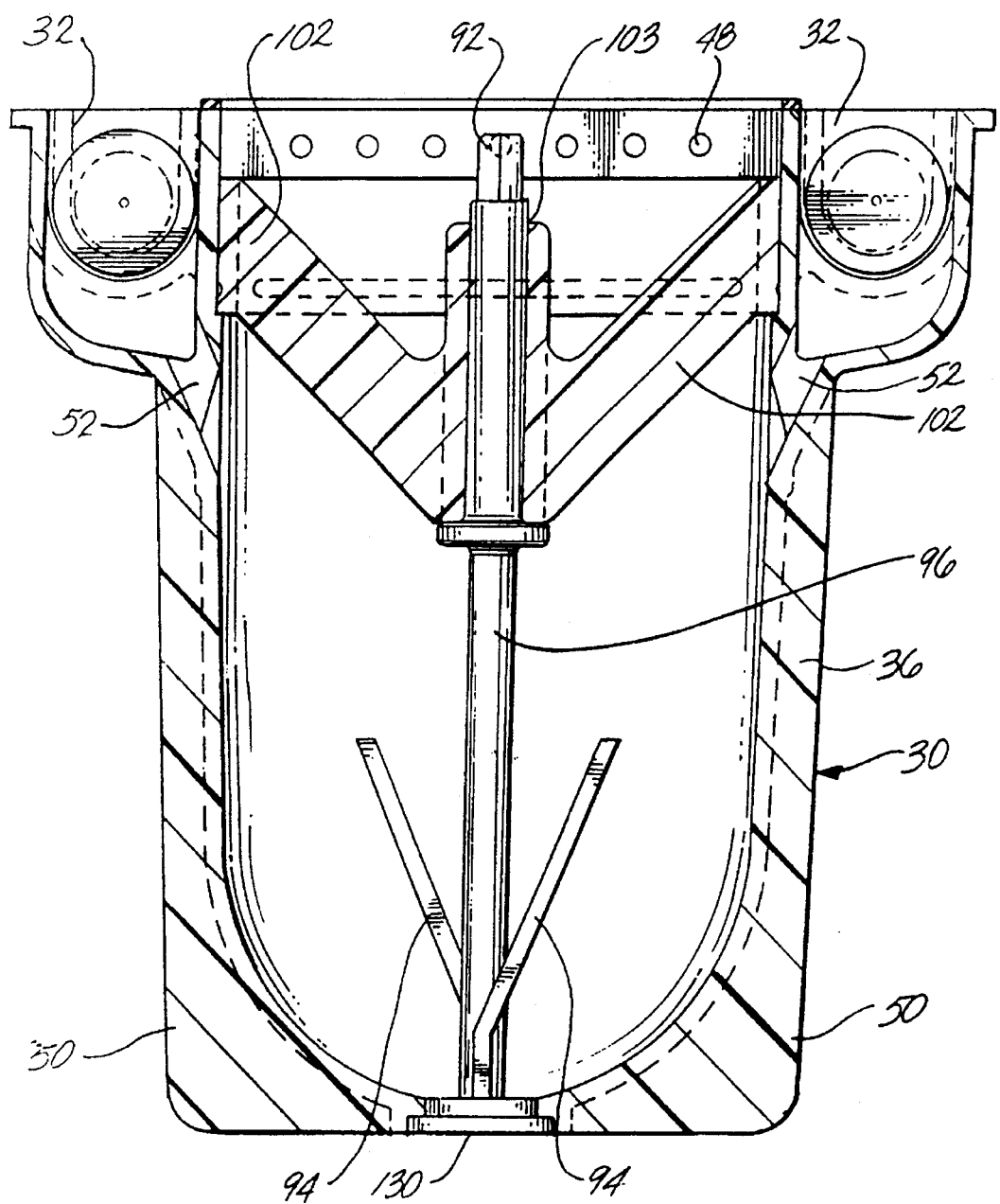

5,531,519

AUTOMATED BONE CEMENT MIXING APPARATUS

CROSS-REFERENCE TO RELATED APPLICATION

This is a division of application Ser. No. 08/088,216 filed Jul. 6, 1993 now abandoned

FIELD OF THE INVENTION

This invention relates to an apparatus for mixing bone cement for use in surgical procedures such as hip replacements.

BACKGROUND OF THE INVENTION

Damage to the joints of the human body, due to arthritis, other degenerative diseases or trauma, often results in the need to replace the joint with a prosthetic device. In the case of hip replacement surgery such devices include a cup which fits into the hip socket, and replaces the acetabulum, and a ball attached to a stem which fits into the femur and replaces the head of the femur. A cement is used to secure the prosthetic devices to the bone.

Currently, the cement used for such replacement is polymethylmethacrylate (PMMA), which requires the use of a catalyst for hardening of the cement. The catalyst, which is supplied in liquid form, must be mixed thoroughly with the methylmethacrylate monomer, and other dry components of the cement, to ensure a complete and even hardening of the cement. Preferably the cement is mixed under a vacuum to prevent air bubbles from being trapped in the cement. Air bubbles in the final cement mix may result in a cement with an undesirably low tensile strength. Typically, mixing of the cement components for between 0.5 to 2 minutes is required to obtain a cement mixture of the desired consistency.

Currently, devices available for mixing of bone cement require hand mixing. This procedure is very laborious and requires a sustained physical effort to complete the mixing process. If the mixing process is not adequate or if the cement hardens before it is delivered, the cement must be discarded and an additional batch prepared. If the process has to be repeated, the surgical procedure, which is under way by the time the cement mixing is commenced, is delayed.

The bone cement is, and should remain sterile, therefore, a "sterile" person is required to perform the mixing and handling of all the sterile components of the cement preparation. With bone cement mixers currently available, a "non-sterile" person is also required, in addition to the "sterile" person, to assist in the setup of the cement mixing apparatus and for handling of all non-sterile components involved in the mixing procedure. At the end of the mixing procedure an additional "sterile" person is often required to assist in the transfer of the cement into cartridges for delivery of the bone cement to the patient. Therefore, preparation of the cement requires at least two and often as many as three people.

The components of the pre-cured cement, methylmethacrylate monomer and catalyst, are irritants and potentially toxic. Therefore, inhalation of the cement components, particularly the monomer, is preferably avoided. Bone cement mixers currently available are not sealed throughout the mixing process and require that the components be manually dispensed into the bone cement mixer, thus exposing the operator to their fumes. These fumes may then be inhaled, for an extended period of time, by all personnel in the vicinity of the cement preparation, making cement preparation irritating and potentially hazardous to their health.

After the cement is mixed, it is poured into a cartridge for dispensing to the site for cementing. At this time, all instruments which have come in contact with the cement must be thoroughly cleaned or discarded.

It is desirable that an apparatus be provided which requires only a single operator to complete all the steps necessary to set-up the apparatus and to mix the cement. It is also desirable that the apparatus isolates all the fumes associated with the cement preparation to thus reduce exposure of hospital workers to these toxic compounds. It is also desirable that such an apparatus be motor driven to avoid the physical endurance required to mix cement and also to ensure reproducible mixing which reduces the need to dispose of cement batches that are unacceptable. It is also desirable that all parts of the device which come in contact with the cement are disposable so that clean-up is minimized.

SUMMARY OF THE INVENTION

A motorized mixer for mixing bone cement for use in attachment of prosthetics and method for using the mixer is described. The mixer comprises a mixing chamber, a liner in the mixing chamber, an impeller within the liner, a motor for driving the impeller and programmable means for regulating the operations of the motor.

In operation dry components of the bone cement are placed in the mixer and vials containing catalyst for the bone cement are placed in vial cavities within the mixer. The mixer is sealed and the vials are broken to release the catalyst into the dry components of the bone cement. The mixer is then started. The mixer runs under the control of a preprogrammed mixing sequence. At the end of the mixing sequence the mixed cement is collected.

In a preferred embodiment of the present invention the preprogrammed mixing sequence comprises applying a vacuum to the interior of the mixer, starting a motor to drive an impeller within the mixer, mixing for a preselected time period, re-applying a vacuum to evacuate fumes from the interior of the mixer and applying pressure to the interior of the mixer to discharge the cement from the mixer.

BRIEF DESCRIPTION OF THE DRAWINGS

Features, aspects and advantages of the invention will be more fully understood when considered with respect to the following detailed description, appended claims and accompanying drawings where:

FIG. 7 is a front view of the bone cement mixer liner taken along the line 7—7 of FIG. 6;

DETAILED DESCRIPTION

Figure 1:
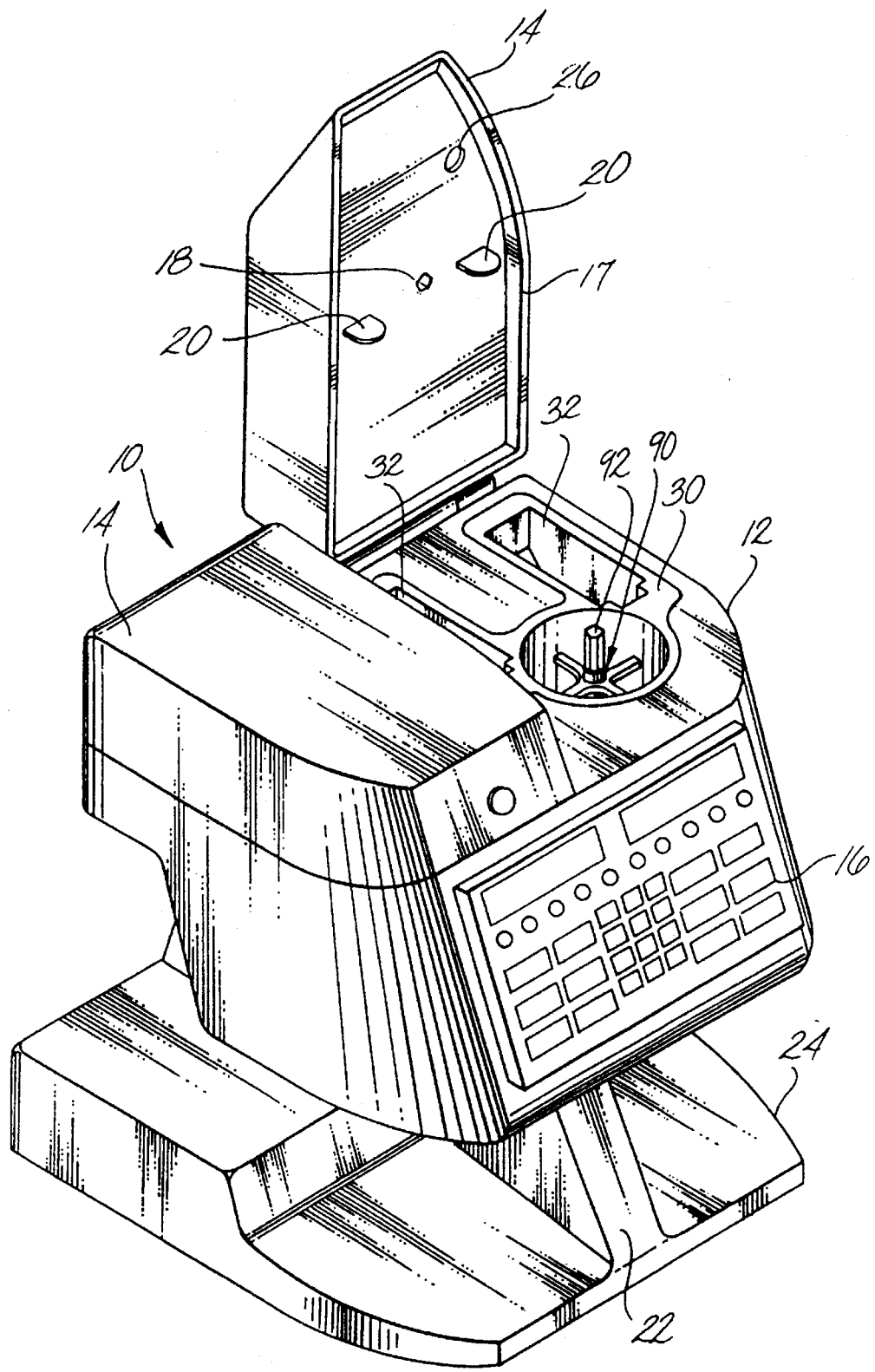
FIG. 1 is a perspective view of one embodiment of a bone cement mixer.
Figure 2:
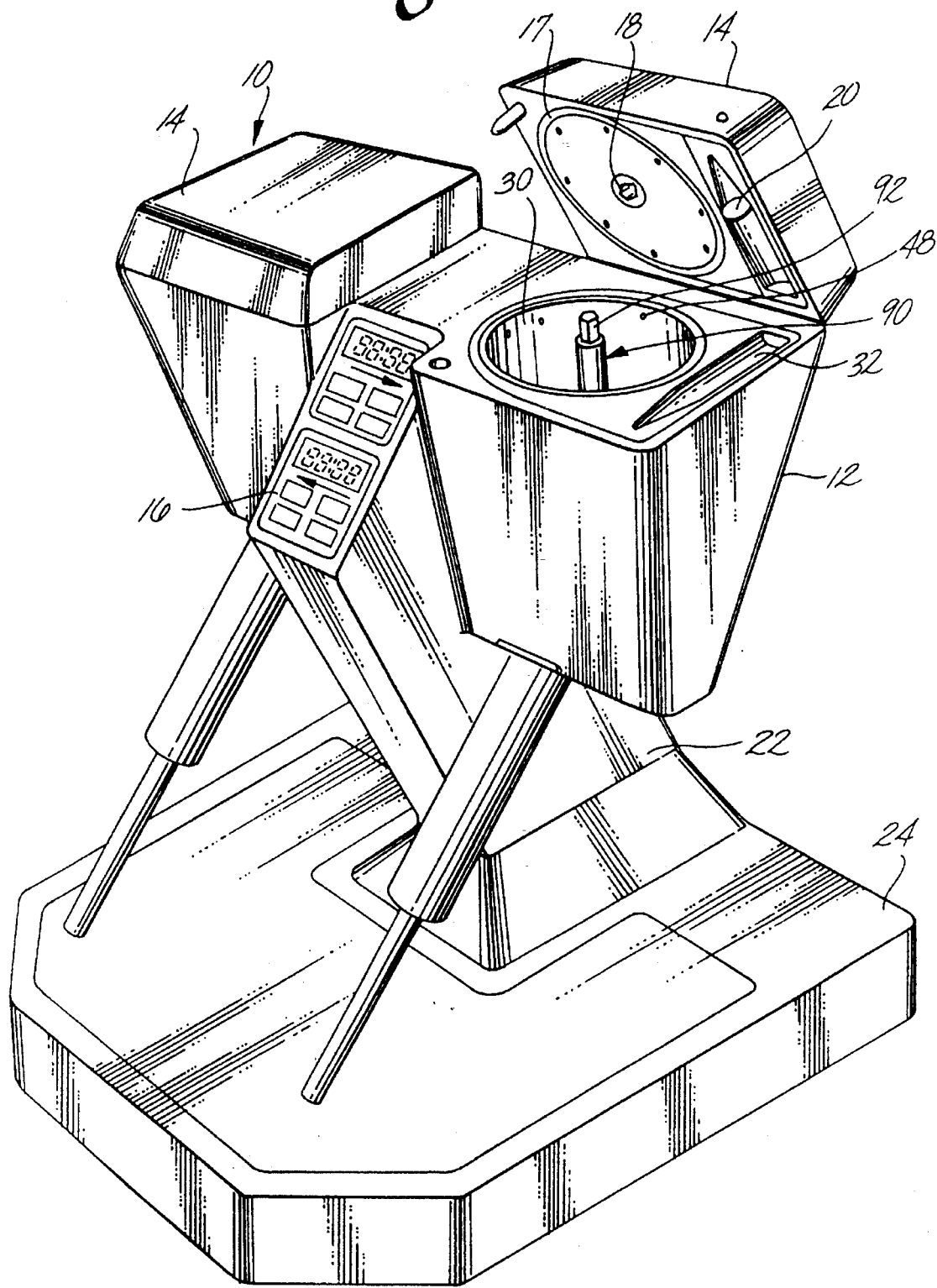
FIG. 2 is a perspective view of another embodiment of a bone cement mixer.

The present invention relates to a bone cement mixer 10, one embodiment of which is illustrated in FIG. 1. A second embodiment of a bone cement mixer 10 is illustrated in FIG. 2 (the same numbers are used for similar parts throughout this description). The bone cement mixer of the present invention has the advantage of being motorized and automated to minimize or eliminate contact, by the operator and others in the surgery, with the components of the cement and fumes generated by the components of the cement.

In general, the bone cement mixer of the present invention comprises a housing 12 which is non-disposable and houses other non-disposable parts of the mixer such as motors, batteries, programmable memory mechanism and a vacuum-pressure pump (not shown). The non-disposable components are sterilized by autoclaving for use. The non-disposable parts of the mixer do not come in direct contact with the cement.

The components which come in contact with the cement are disposable and are supplied as a cement mixing kit, which comprises a liner 30, which fits into the housing and comprises the necessary mixing impeller 90 for mixing the cement. Other disposable components of the kit include a cement injector gun or adapters into which the mixed cement is collected at the end of the mixing procedure. The disposable components of the mixer are supplied in kit form which are supplied as pre-sterilized. The individual components of the bone cement mixer are described in detail below.

In operation, liner 30 (see FIGS. 3–8, described in detail below) is placed in the mixer housing 12 and an injector gun or adapters (not shown) are placed on the cement outlet of the mixer. Components of the cement, such as the powder which includes the methylmethacrylate monomer are then placed in the liner. Vials containing catalyst, for the hardening of the cement, are placed in vial cavities 32 located in the liner. The bone cement mixer is then programmed for the desired mixing time. Lid 14 of the housing is then closed to seal the components of the cement within the mixer. Closing the lid also results in breaking of the vials thus releasing the catalyst into the other cement components (see below for a detailed description). A vacuum is applied to the interior of the liner to prevent the formation of air bubbles in the cement as it is mixed and also to remove fumes generated from the components of the cement. After the bone cement mixer has been evacuated the mixer is started.

At the end of the preselected mixing time, the mixer stops automatically and, in one embodiment of the present invention, sounds an alarm to alert the operator. A vacuum is again applied to the chamber to evacuate fumes which have built up during the mixing procedure. When the mixing is completed, the vacuum is released and pressure is applied to the chamber to evacuate the cement from the mixer by pushing the cement through a port located at the bottom of the mixer into a cement gun or various cartridges for dispensing the cement. The disposable portions of the mixer, i.e., the liner, can then be removed from the mixer housing and discarded after use. The components of the mixer and its operation are described in detail below.

The mixer housing 12 (FIGS. 1 and 2) comprises a pair of lids 14 which are attached to a housing body by a hinge (not shown) or other suitable means of attachment. The lids each house a motor (not shown) that supplies the power for mixing. Motors suitable for use in the present invention are motors such as conventional gear motors, pancake motors or the like. The motors are preferably reversible so that mixing can be performed by mixing in one direction for a period of time and then in the opposite direction, if desired, to ensure complete mixing of the cement. Motors suitable for use in the present invention are gear motors such as those sold by Globe of Dothan, Ala., Model Number 407A6008-2, which is a 12 V, 120 rpm, reversible motor.

In one embodiment of the present invention the motor is controlled by a current sensing mechanism. When the current required to operate the mixing motor exceeds a preset level, the device automatically terminates the mixing cycle, sounds an alarm and begins evacuation the cement from the mixer. This mechanism, therefore, indirectly senses the viscosity of the cement to ensure the cement is evacuated before it becomes too viscous to flow from the mixer and also prevents overmixing of the cement which would result in the cement hardening too quickly.

In a preferred embodiment, the motorized mixer of the present invention is programmable so that different cement consistencies and/or compositions can be mixed effectively. For example, cement for tibial/acetabulum replacement surgery is generally preferred at a thick or viscous consistency and mixing of the cement components for about two minutes generates a suitable cement for this application. Cement for femoral application is generally preferred at a thinner or less viscous consistency than tibial/acetabulum cement, because it has to be placed within the femur. Mixing of the cement components for about one minute generates a suitable cement for this application. Moreover, some bone cements require a "stop period" during mixing so that the cement may "set up" properly. These mix requirements could be placed in the "permanent" memory of the mixer. Alternatively, a "custom" mix program could also be programmed by the user. Suitable programmable memory mechanisms are well known in the art and suitable devices for use in the present invention are devices such as Model No. 8748 sold by NEC or other similar devices sold by other manufactures of programmable controllers. The programmable controllers are included within the housing. In another embodiment of the present invention the "program" is "hard wired" using non-programmable analog and digital components rather than incorporated into a programmable memory mechanism.

Figure 23:
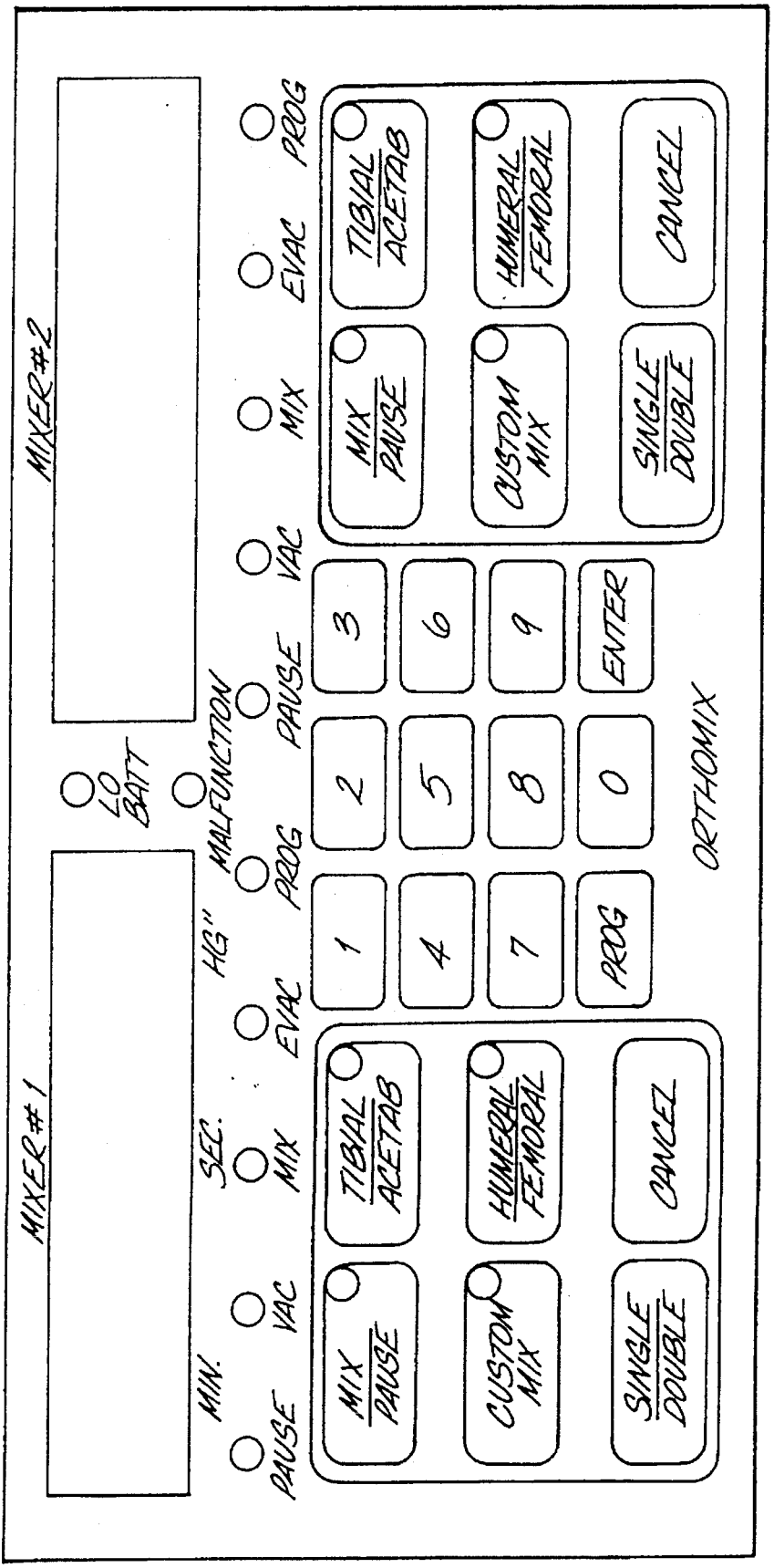
FIG. 23 is a front elevation of a key pad.

Located on the front of the mixer housing is a key pad 16 (see FIG. 23). The key pad may include a display which displays mixing time elapsed and the level of vacuum or pressure within the chamber. Also, buttons which allow for programming such functions as mixing, pausing the mixing, applying and releasing vacuum and selecting a program option may be included. Additional buttons may be included which allow the selection of a preprogrammed or custom mix protocol and re-setting the mixer program. The key pad may also include LED's to indicate the phase of the mixing cycle the mixer is currently executing and segmental LED's may be included to indicate the mixing time elapsed and the vacuum level within the chamber. LED's suitable for use in the present invention are made by Kingbrite or "mil-spec" high temperature resistant LED's made by Hewlett-Packard. Key pads suitable for use in the present invention include membrane key pads which have an overlay such as a multi-layer polycarbonate, such as those sold by 3M, or a silicone rubber.

When a custom mix is chosen the program parameters may also be specified using the key pad. In one embodiment the key pad for custom mixing times includes a group of switches which are identified as numbers 0-9 for specifying mixing times. Included in the group of switches are switches to enter the program. Also located on the key pad is an alarm to indicate that a mix procedure has been completed. Lights can also be included to indicate that power is being supplied to the mixer.

In one embodiment of the present invention power for the mixer is supplied by batteries which are included within the housing. Batteries suitable for use in the present invention are rechargeable nickel-cadmium batteries (12 V, 2.8 Amp). These batteries will typically run the mixer for three mixing cycles prior to requiring recharging. In an alternative embodiment of the present invention the mixer can be connected to A.C. power by use of a D.C. transformer. Such transformers are well known in the art. When batteries are used as a source of power, a "low battery" indicator light is also included on the key pad.

Also included within the housing is a vacuum-pressure pump for evacuating the interior of the liner during mixing. Pumps suitable for use in the present invention include diaphragm pumps such as those made by ASF Inc. of Norcross, Ga., which draw about 70 cm of mercury in vacuum mode and generate 100 psi in pressure mode of operation, used in combination with solenoid valves such as those sold by Humphrey Valve Co. of Kalamazoo, Mich. and vacuum transducers, made by Omega of New York, N.Y., which provide a sensing mechanism to control and maintain the desired pressure level. The solenoid valves are chosen to operate in a range of about 0-76 cm of mercury in vacuum mode and up to 120 psi in pressure mode of operation.

To sterilize the mixer for use the housing is autoclaved. Since the housing includes the vacuum-pressure pump, the program controller, batteries and motors within the housing, which are not readily removable, the housing also includes shielding for these components to prevent them from being exposed to the high temperatures experienced during autoclaving. Suitable shielding is provided by encasing the heat sensitive components in protective "cans" made of materials such as glass-filled FORTRON grade of polyphenyline sulfide, such as that sold by Hoechst Celanese of Chatham, N.J. (which is suitable for use at temperatures up to about 280° C.) EKTAR, a 15% glass filled thermoplastic co-polymer resin sold by Eastman Performance Plastics of Kingsport, Tenn. (which is suitable for use at temperatures up to about 255° C.) or ULTEM sold by General Electric.

On the underside of each lid 14 is a seal 17 which seals against the housing when the lid is closed. Also located on the underside of each lid is a drive socket 18, which connects the motor to a paddle or impeller shaft 92 of the liner. The end of the shaft has, in a preferred embodiment, a pentagonal cross section to prevent slippage between the shaft and drive socket. While a pentagonal shape is preferred, it is understood that other shapes such as triangular, square and hexagonal would also be suitable.

Also located on the underside of the lid are blades 20, so that when the lid is closed, the blades extend into vial cavities 32 of the liner to break and thereby open vials contained in the vial cavities.

The housing body comprises a pair of chambers into which liners are placed (the chambers are shown with the liners in place). Each of the chambers are open at their bottom (not shown) to allow the liner to extend to the exterior of the housing and for the attachment of cement collection adapters. O-rings are located around these openings to seal the liner in place.

The housing body is preferably mounted on a stand 22 projecting upward from a broad horizontal base 24 that provides support for the housing. The housing is preferably made from a high temperature plastic material such as ULTEM, made by General Electric, or VECTRA made by American Celanese Corp. However, areas that may come in contact with the cement, such as the area directly under the mixing chambers, are preferably made from, or coated with, a material such as stainless steel which can be easily cleaned to remove any cement that may be spilled during the preparation of the cement.

In one embodiment of the present invention (FIG. 1), a vacuum-pressure port 26 is also included in the lid. The vacuum port is connected to the vacuum pump, located in the housing of the mixer, by pressure resistant or vacuum tubing. The vacuum may also be connected to a "house" vacuum line as well as, or in place of, the vacuum pump. In another embodiment (FIG. 2), multiple vacuum-pressure holes 48 are located around the periphery of the liner. These holes communicate with a manifold in the liner that is connected to the vacuum pump and/or house vacuum line. In another embodiment vacuum/pressure holes 31 (FIG. 3) are provided in the liner at the ends of the vial cavities. In this embodiment the holes attach to a manifold in the housing, and communicate with the chamber of the liner via cavities placed in the lid (not shown).

Liner 30 of the present invention, illustrated in FIGS. 3-8, is made from materials such as polyethylene, and can be discarded after use.

In general, the liner comprises a cup shaped chamber 36 which forms a well of generally circular cross section, into which the components of the cement are placed for mixing. Located at the top of the liner, and at one or both sides, are vial cavities 32 into which are placed vials which contain the liquid catalyst for the cement. At the bottom of the liner is a port 130 for collecting the cement at the end of the mixing procedure. An impeller 90 is provided within the liner for mixing the cement.

In one embodiment of the present invention (see FIGS. 6–8) ribs 50 are placed along the outside of the liner and at its bottom that act to strengthen the liner and inhibit its collapse under the desired operating vacuum. In this embodiment of the present invention four ribs are placed around the outside of the liner and are equally spaced from each other. Matching grooves can be placed in the walls of the housing chambers, into which the liners are dropped, so that the ribs can act to align the liner within the housing. However, the ribs may result in stress risers with extended use or at high vacuum/pressure.

In one embodiment of the present invention the liner is evacuated via vacuum port 26 located in lid 14. In another embodiment (see FIGS. 6–8) a port 46 is located in the liner for connecting the liner to the vacuum-pressure pump. A series of holes 48 are located in the liner, in close proximity to the vacuum port connector and open to a manifold that is connected to the vacuum port. These holes allow the interior of the liner to be evacuated and vented as needed.

Figure 3:
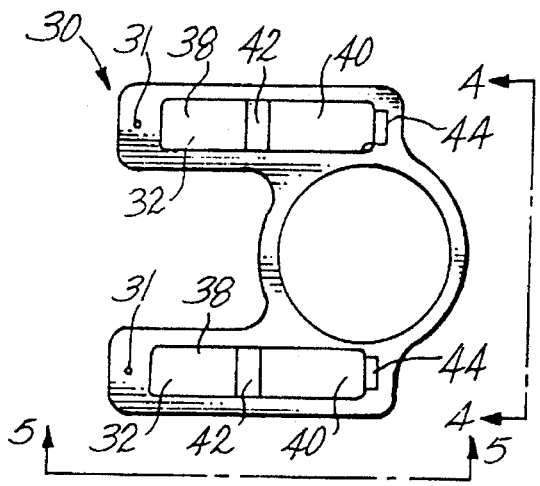
FIG. 3 is a top view of a one embodiment of a bone cement mixer liner.
Figure 4:
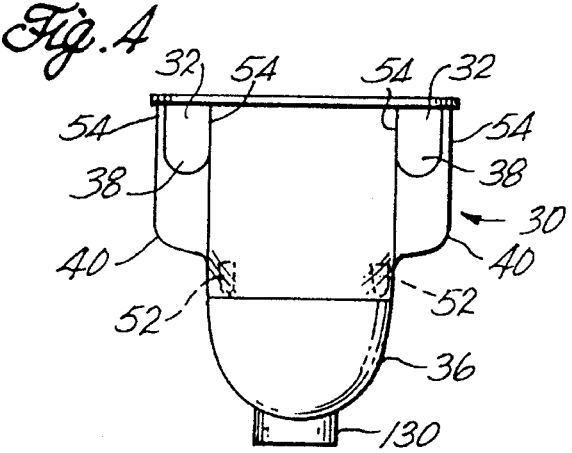
FIG. 4 is a front sectional view of the bone cement mixer liner taken along the line 4—4 of FIG. 3.
Figure 5:
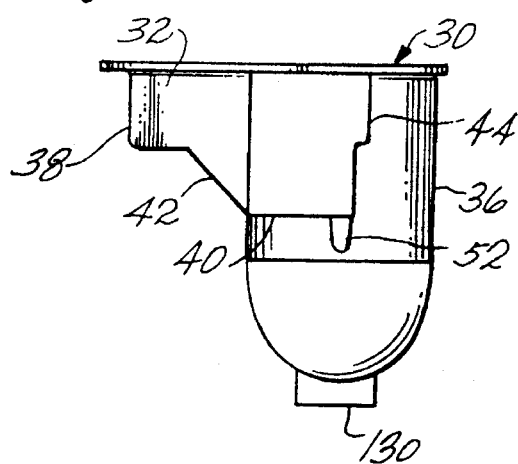
FIG. 5 is a side sectional view of the bone cement mixer liner taken along the line 5—5 of FIG. 3.

Vial cavities 32 in one embodiment of the present invention (FIGS. 3–5) comprise a shallow section 38 and a deep section 40 which are connected by an angled floor 42. In operation, vials containing catalyst, are placed in the vial cavity in an horizontal position, resting at one end on the floor of the shallow section and at the other end on a shelf 44 that is at the same level as the floor of the shallow section and above the floor of the deep section. A single vial is placed in one vial cavity when a single batch of cement is to be mixed or, in those embodiments with two vial cavities per cup shaped chamber, vials are placed in each of the two vial cavities when a double batch of cement is to be mixed. The vial cavities are located in a position on the liner so that, when the lid of the mixer is closed, the blades penetrate into the vial cavities, thus rupturing the neck of the vials in the vial cavities. In the embodiments of FIGS. 3–5, the rupturing also results in the vial being upended into the deep section of the vial cavity and ensures complete emptying of the contents of the vial.

Figure 6:
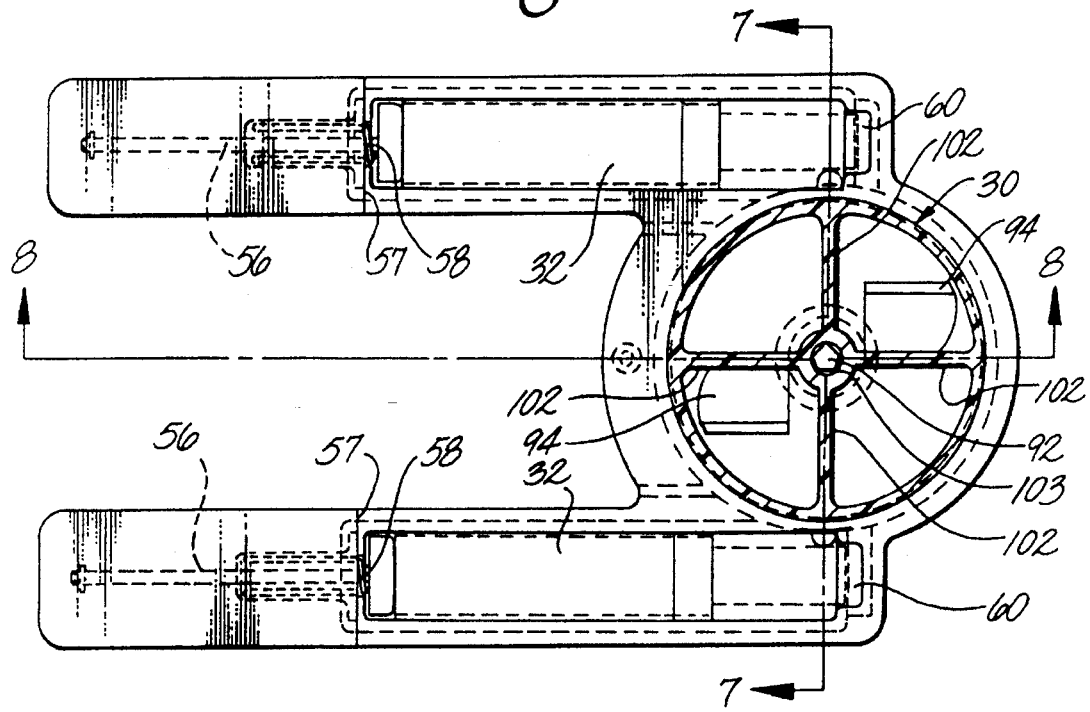
FIG. 6 is a top view, partly in section, of another embodiment of a bone cement mixer liner.
Figure 8:
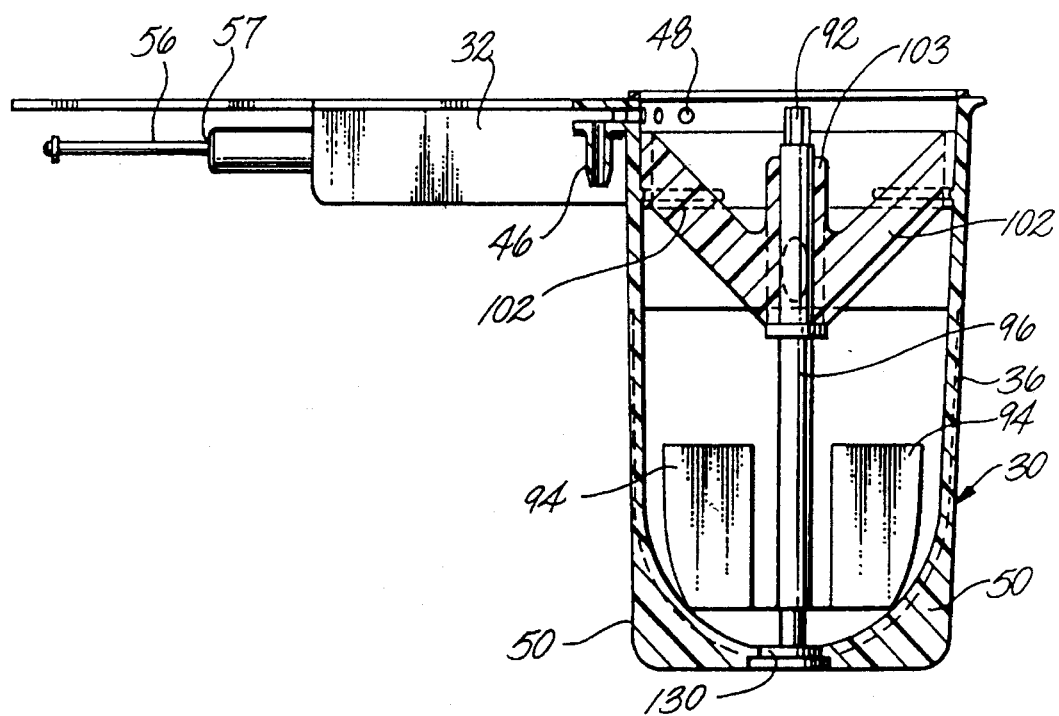
FIG. 8 is a side view of the bone cement mixer liner taken along the line 8—8 of FIG. 6.

Catalyst is commercially available in different sized vials, which have different lengths. Therefore, it is preferable that the vial cavity is able to accommodate the different sized vials. In the case of the long vial, the vial cavity is of a dimension such that a long vial will fit snugly into the vial cavity. When a shorter vial is used, the vial is held by the close fit of the liner side walls 54 (FIGS. 3 and 6).

In another embodiment, a mechanism (see FIGS. 6–8) which comprises a plunger 56 is used to hold the small vial in place. The plunger extends along the length of the vial cavity and through an end 57 to the exterior of the vial cavity. The plunger is attached to a spring 58. When the vial cavity is empty, the plunger contacts the end wall 60 of the cavity and the spring is relaxed. When the plunger is pulled away from the end of the vial cavity, the spring is compressed and a small vial can be placed in the vial cavity. The plunger, with the force applied by the spring, holds the vial in place and at the end of the vial cavity. When a large vial is used, the plunger is drawn back along the full length of the vial cavity, to allow the large vial to be placed in the vial cavity.

In another embodiment of the present invention (not shown), a tension spring is used to hold the vial in the vial cavity. In this case a shorter plunger is attached to a tension spring. The spring is attached to end wall 60 of the interior of the vial cavity. When the plunger is drawn back to accommodate a vial, the spring is stretched and applies a force to the plunger which in turn secures the vial in place.

When the lid is shut, the vial is ruptured and the liquid contents of the vial are released and flow through a duct, into the liner chamber where they are mixed with the other components of the cement.

In each embodiment of the present invention, the vial cavities are connected to the liner chamber by a duct 52. In a preferred embodiment of the present invention, a screen is located in the duct to prevent any glass slivers, that may result from the rupturing of the vial, from entering the cement mixture.

Figure 9:
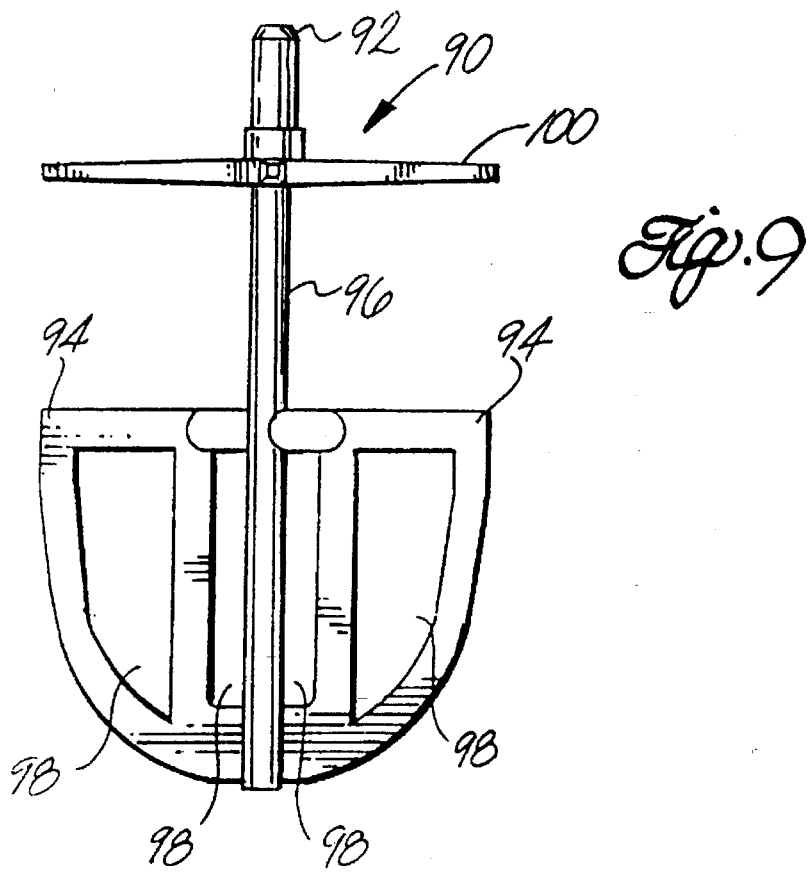
FIG. 9 is a front view of one embodiment of an impeller for use in the present invention.
Figure 10:
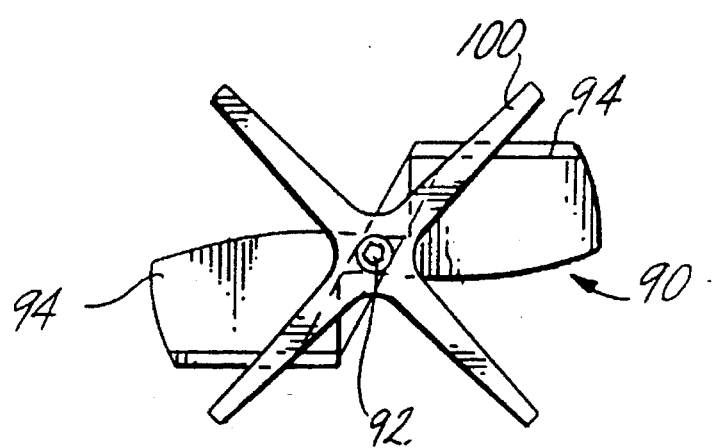
FIG. 10 is a top view of the impeller illustrated in FIG. 9.

In the interior of the liner is a mixing impeller. In one embodiment of the present invention (see FIGS. 9 and 10) the impeller comprises two blades 94 extending from opposite sides of a shaft 96. The blades are bent at an angle of about 45° so that the extremities of the two blades are approximately parallel to each other (see FIG. 10). When viewed from the side (see FIG. 9) the blades form a roughly semicircular shape to conform to the shape of the interior of the liner. In one embodiment of the present invention the blades include "cut-out" sections 98 which reduce the amount of blade which comes in contact with the cement thus reducing cement loss.

At the top end of the shaft is a cross-shaped member 100 which centers the shaft, and the blades, when the impeller is placed in the liner. In a preferred embodiment of the present invention the top sides of the cross-shaped member are rounded to inhibit cement powder collecting on its tops when the cement powder is introduced into the liner. On the top of the shaft in the center of the cross-shaped member is shaft 92 which connects to the drive of the motor when the lid is closed. The end of the shaft comprises a generally pentagonal shaped projection for mating with the pentagonal shaped cavity of the socket.

In another embodiment of the present invention (see FIGS. 6–8), two pairs of arms 102 of an impeller bearing extend across the interior of the liner. Each of the arms is placed at 90° to each adjacent arm and is attached at one end to a centrally located cylindrical bearing 103. The arms are slanted downward to form a "V" shape. The outer ends, and the upper part of the "V", attach to the liner body. The powder components of the cement are introduced into the liner by pouring them around the arms and into the well of the chamber of the liner. The downward slant of the arms prevents the powder from collecting on the arms.

At the intersection of the arms and extending upwardly through cylindrical bearing 103, in the center of the liner, is a shaft 96 which connects to the drive of the motor when the lid is closed. The end of the shaft comprises a generally pentagonal shaped projection for mating with the pentagonal shaped cavity of the socket. It is desirable that the end of the shaft does not contain any cavity or other structure that could collect powder as the powder in introduced into the liner. When the lid is closed the shaft connects with the socket and thus the drive of the motor. The matching pentagonal shapes of the shaft and the socket prevent the drive shaft slipping relative to the socket. Again, while a pentagonal shape is preferred, it is understood that other shapes such as triangular, square and hexagonal would also be suitable.

At a lower end of the mixer shaft 96 are paddles 94. When the mixer shaft is turned by the action of the motor the paddles move through the cement components thereby mixing them.

Figure 11:
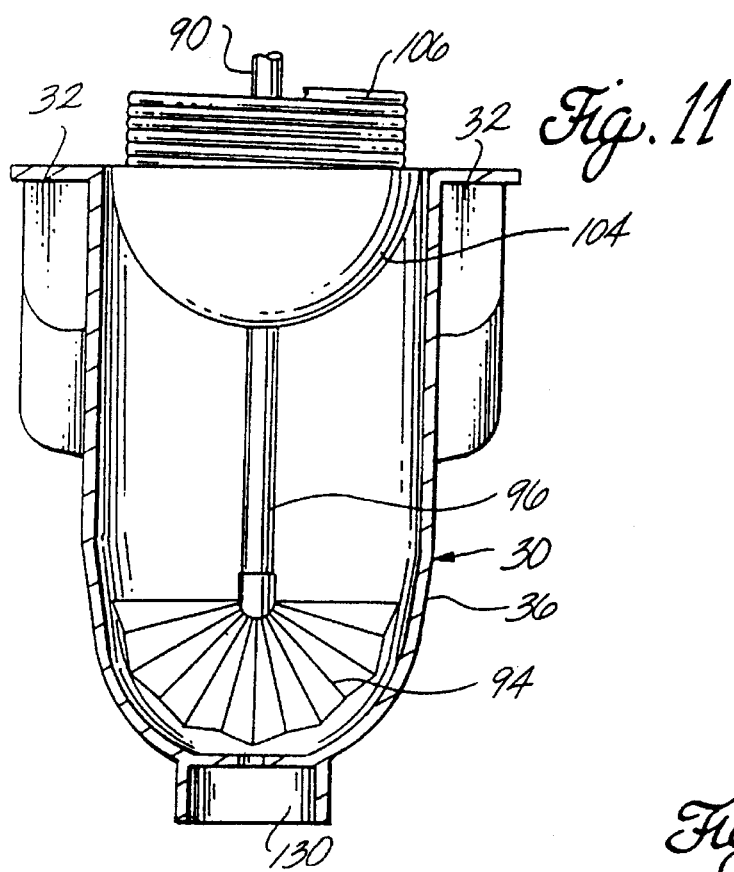
FIG. 11 is a front view of another embodiment of an impeller for use in the present invention in position for mixing.
Figure 12:
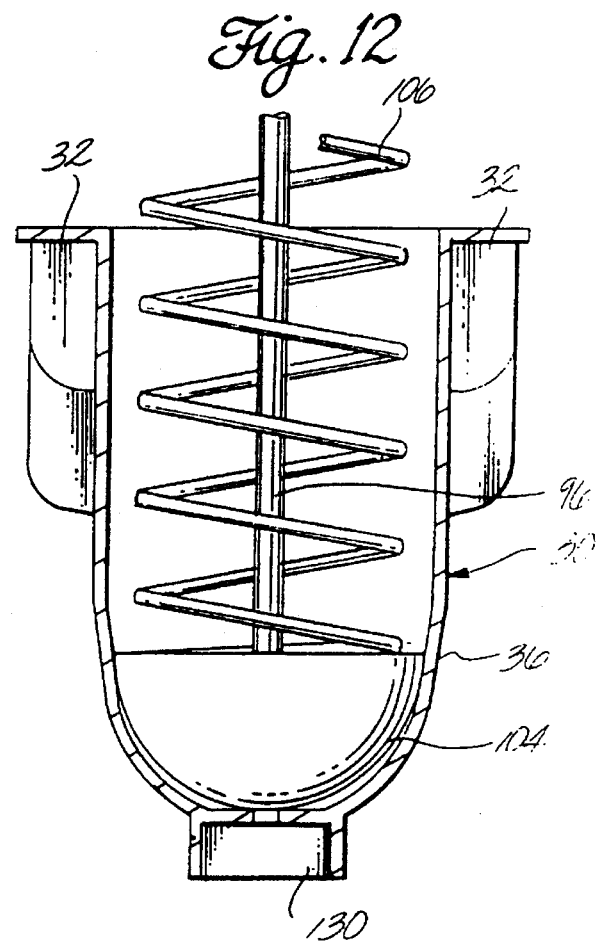
FIG. 12 is a front view of a collapsible paddle and a plunger of FIG. 11 in position for evacuation.

In another embodiment of the present invention (see FIGS. 11 and 12) a liner comprises a paddle which is collapsible. The paddle 94 is of a fan-like construction. In this design the collapsing of the blade is desirable since a plunger 104 is used to force the cement out of the liner when the mixing procedure is complete. In this embodiment of the present invention the plunger is moved to the bottom of the liner by the action of a spring 106. The spring is coiled during the mixing procedure and is released when the mixing is completed.

It should be noted that at all times during the preparation of the cement, i.e., from the time the lid is closed, the chamber of the mixer is sealed and fumes from the contents of the chamber are unable to escape. Also, during the mixing procedure a vacuum is applied which, on one hand prevents the formation of air bubbles in the cement and on the other hand removes fumes from the chamber, preferably through the house vacuum line. Thus the room in which the cement mixing procedure is performed remains relatively free of the irritating and potentially toxic fumes which are normally associated with the preparation of cement. It is only at the completion of the mixing procedure that the chamber is opened, at its bottom, to allow the cement to flow from the chamber of the liner into a cartridge.

The vacuum applied to the interior of the liner during mixing is preferably about 55 cm of mercury. If a "stronger vacuum" is used the components of the cement may "boil" or evaporate and the liner may implode. A "weaker vacuum" may be insufficient to "degas" the cement during mixing.

At the completion of the mixing procedure a vacuum is again drawn in the interior of the chamber to evacuate any fumes that have been generated during the mixing cycle. The vacuum is then "released" and positive pressure is applied to the interior of the liner. The cement is then allowed to flow from the liner through a port at the bottom of the liner. As noted above, in one possible alternative embodiment, a plunger is used instead of or in addition to the positive air pressure to dispense the cement through the bottom port. The cement is collected into cartridges or syringes for dispensing the cement.

Figure 13:
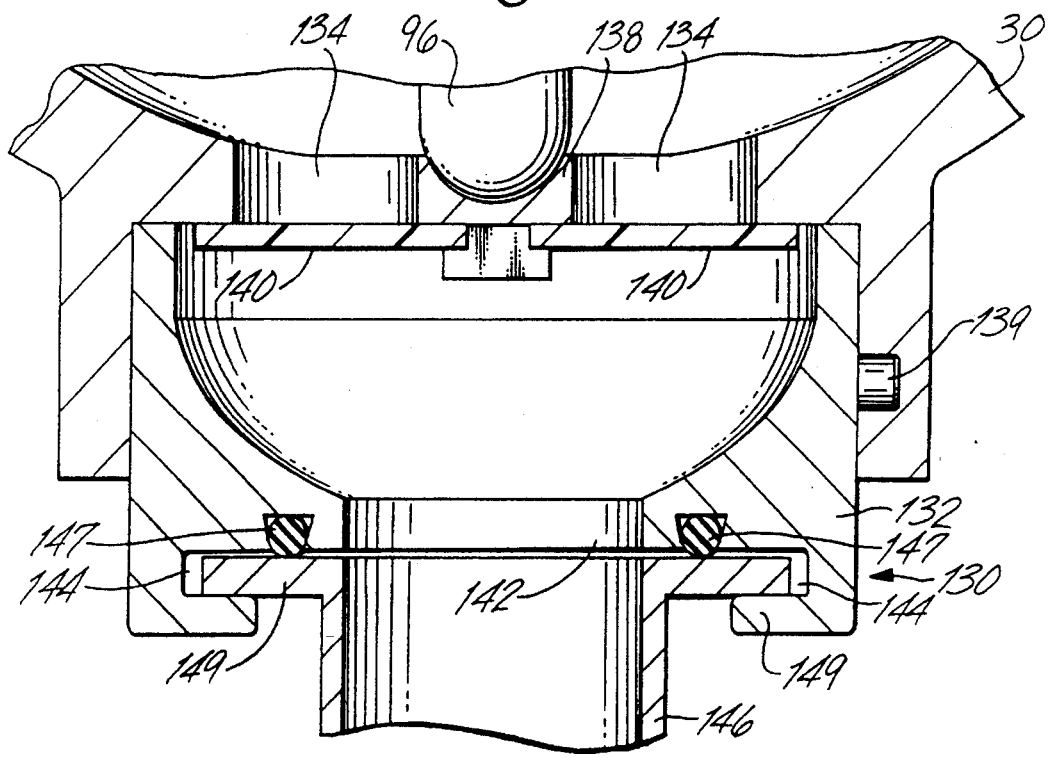
FIG. 13 is a side view of one embodiment of a port in the liner, shown in the closed position.
Figure 14:
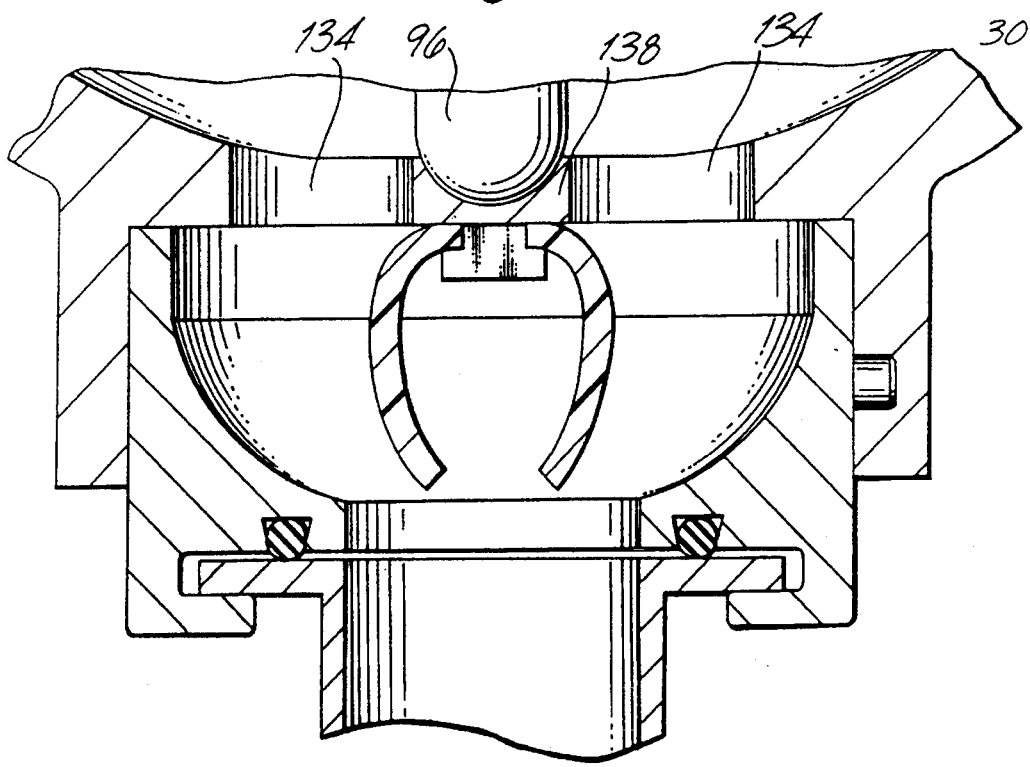
FIG. 14 is a side view of the port of FIG. 13, shown in the open position.

In one embodiment of the present invention, the port 130 (as illustrated in FIGS. 13 and 14) for removing the cement from the liner comprises a generally cylindrically shaped member 132. At one end of the cylinder is an aperture 134 comprised of multiple openings which mates with an aperture of the liner. In one embodiment of the present invention the cylindrically shaped member is attached to the liner by a "bayonet" type fit 139 (see FIGS. 13 and 14). In another embodiment the cylindrically shaped member is attached to the liner by welding.

The aperture 134 encloses an open grid. In the center of the grid is an attachment point 138, to which is attached a membrane 140, on the under side of the grid. When a vacuum is drawn in the chamber (see FIG. 13) the membrane is drawn flat against the aperture forming a seal. At the end of the mixing cycle, when pressure is applied to the chamber, the membrane is deflected away from the aperture allowing cement to flow out through the aperture (see FIG. 14).

At the opposite end of cylinder 132 is a second aperture 142. At the base of the second aperture is a attachment means which comprises two parallel slots 144 which run across the interior of the cylinder. The slots allow attachment of a detachable cement collection means 146 to be attached to the liner for collection of the cement after mixing. The collection means comprises flanges 149 which slide into slots 144. The collection means is held in place and sealed against the cylinder 132 by O-ring 147.

In another embodiment of the present invention, port 130 (see FIGS. 15 and 16) comprises a slide mechanism 153, and attachment means for the attachment of a cement collection device to the liner is similar to that described above. Flanges on the top of a cartridge adapter slide into slots (as illustrated in FIGS. 13 and 14) attached to the bottom of the mixer housing. As an adapter is pushed into place, it abuts lever 152 and slide 60 is pushed away from a liner plug 154 located at the bottom of the mixer chamber, aligning aperture 155 with the liner plug.

Figure 15:
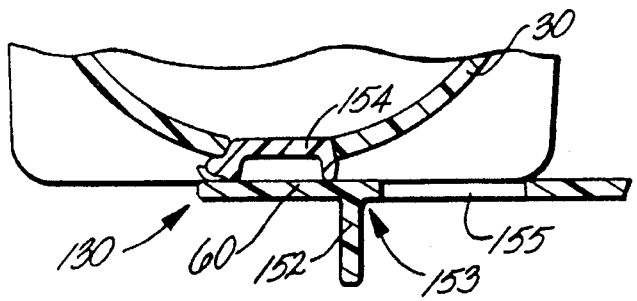
FIG. 15 is a side view of another embodiment of a port in the liner, shown in the closed position.
Figure 16:
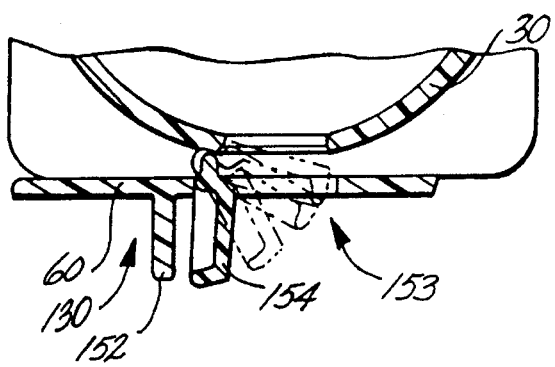
FIG. 16 is a side view of the port of FIG. 15, shown in the open position.

The port is in a closed position, as shown in FIG. 15, during the mixing procedure and is held in the closed position by slide 153. During mixing the port retains the components of the cement within the liner chamber. At the end of the mixing process, a cartridge is slid into place, pushing the slide away from the plug, the vacuum is "released" and positive pressure is applied to the liner chamber to thereby open the plug and force the cement to flow into cartridges for dispensing.

Figure 17:
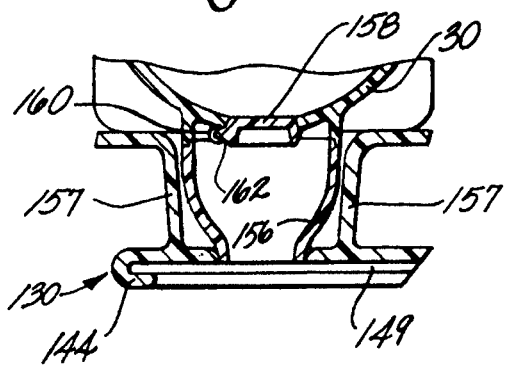
FIG. 17 is a side view of another embodiment of a port in the liner, shown in the closed position.
Figure 18:
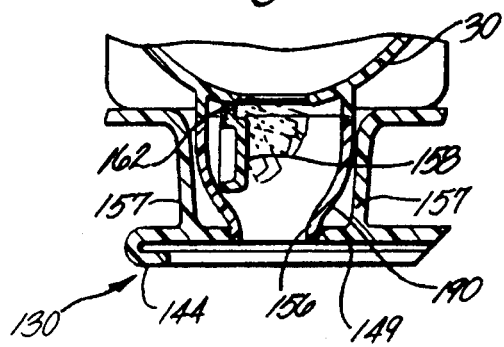
FIG. 18 is a side view of the port of FIG. 17 in the open position.

In another embodiment of the present invention, illustrated in FIGS. 17 and 18, the bottom of the mixer comprises a slot which is offset, by walls 157, from the main body of the mixer housing. The slot is similar to that described above. In this design the liner, which fits into the mixing chamber, has a bell shaped port 156 at its bottom end. At the top of the port is a plug 158 which is contiguous with the floor of the liner, when in the closed position. In the closed position the components of the cement are retained in the liner and there is no "dead space" into which powder or liquid components could become trapped and thereby, not mixed. The plug is held in place by the vacuum which is applied during the mixing process and by a "crush rib" 160 on a hinge 162 which attaches the plug to the liner.

When the mixing of the cement is complete the vacuum is released and positive pressure is applied to the inside of the liner. This positive pressure forces the plug out of the liner and allows the cement to flow from the liner and into cartridges attached to the bottom of the mixer. The cement is collected in the cartridges which can then be fit into a cement injection gun for dispensing as required.

Dispensing of the cement is performed by placing the cement into a cartridge that fits onto a cement injection gun, such guns are well known in the art. The cement injection gun is then used to deliver the cement to the surgical site as required. Many different designs of cement injection guns, and cartridges designed to fit them, are available. The cartridge designs differ depending on the manufacturer of the cartridge and the use for which the cartridge was designed. Some cartridges have screw tops while others have handles and flanged tops and many of the available cartridges have different diameters. Some cartridges have long nozzles, such as those designed to deliver cement to the femur, while others have relatively short nozzles. In one embodiment of the present invention, an adapter 190, which will fit all, or most of the available cartridge designs, is used to attach the cartridge to the mixer.

Figure 19:
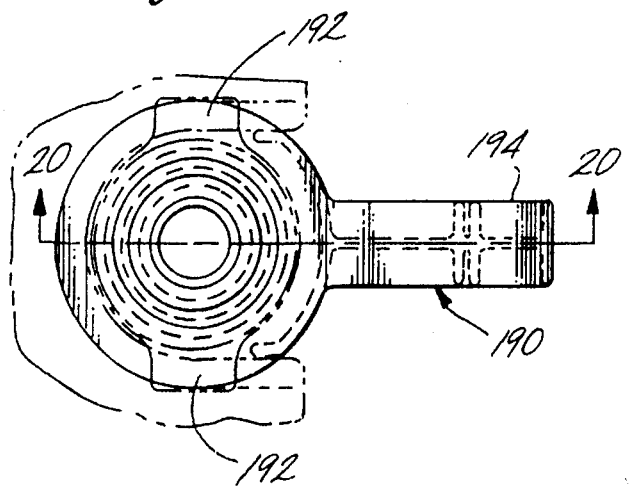
FIG. 19 is a top view of one embodiment of an adapter for cement dispensing cartridges.
Figure 20:
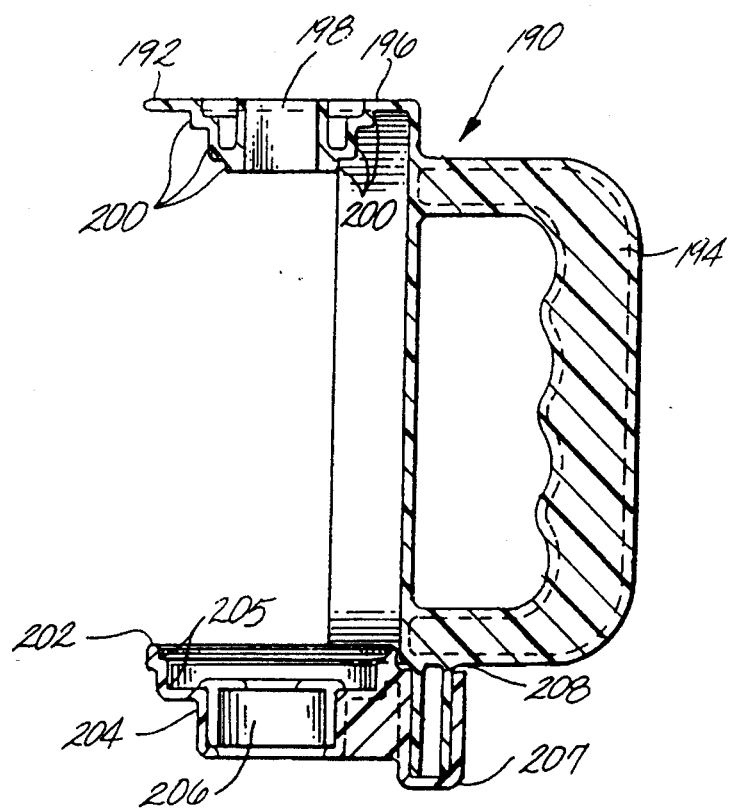
FIG. 20 is a side view of the adapter taken along line 20—20 of FIG. 19.

In one embodiment of the present invention, shown in FIGS. 19 and 20, cartridge holder or adapter 190 comprises a handle 194 attached at a top end to a top brace 196. The top brace comprises a central bore 198 through which the cement can flow from the mixer into a cartridge held in place by the adapter. The central bore is formed by a tube. On an upper side of the outer diameter of the tube are attached flanges 192 which attach the cartridge adapter to the mixer by sliding into slots 210 (illustrated in FIGS. 21 and 22) on the bottom of the mixer housing. The outer surface of the tube is stepped 200 to form different sized diameters. Each of the different diameters is chosen to fit an internal diameter of a tubular cartridge. Thus the cartridge is attached to the top brace by pushing the cartridge over the appropriately sized diameter step thus forming a friction fit which holds the cartridge in place. The step also centers the cartridge below the bore so that cement can be delivered into the cartridge.

A bottom brace 202 comprises a ring 204, the internal diameter of which is stepped 205 to accommodate the outside diameter of the various tubular cartridges that are commercially available. A central bore 206 in the ring allows different types of cartridges, such as those with long nozzles, to be fitted into the bottom brace. A thimble shaped member 207 is attached to the outer perimeter of the ring. The ring is attached to the handle by forcing the thimble shaped member over a projection 208 attached to the base of the handle. When the bottom brace is attached to the handle, a cartridge is held securely in place.

Figure 21:
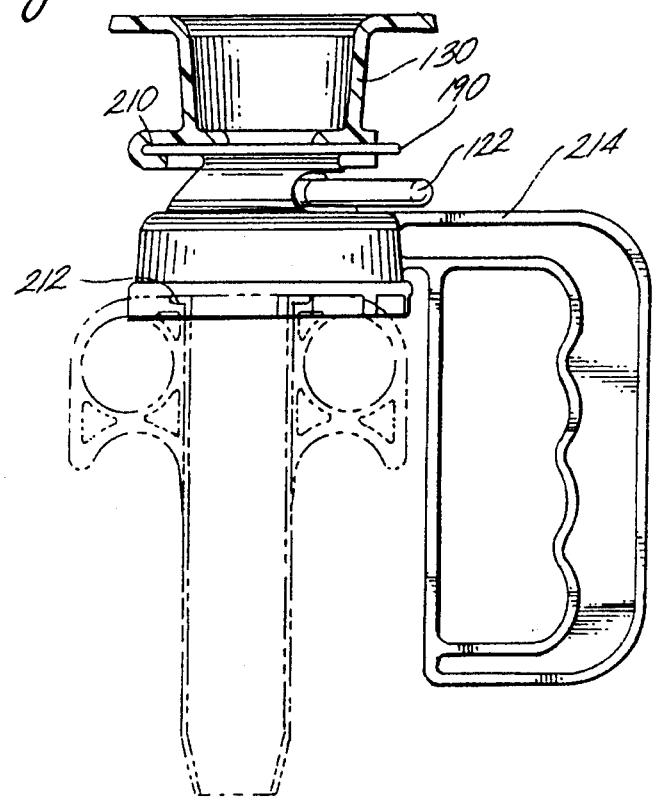
FIG. 21 is a side view of another embodiment of an adapter for cement dispensing cartridges.
Figure 22:
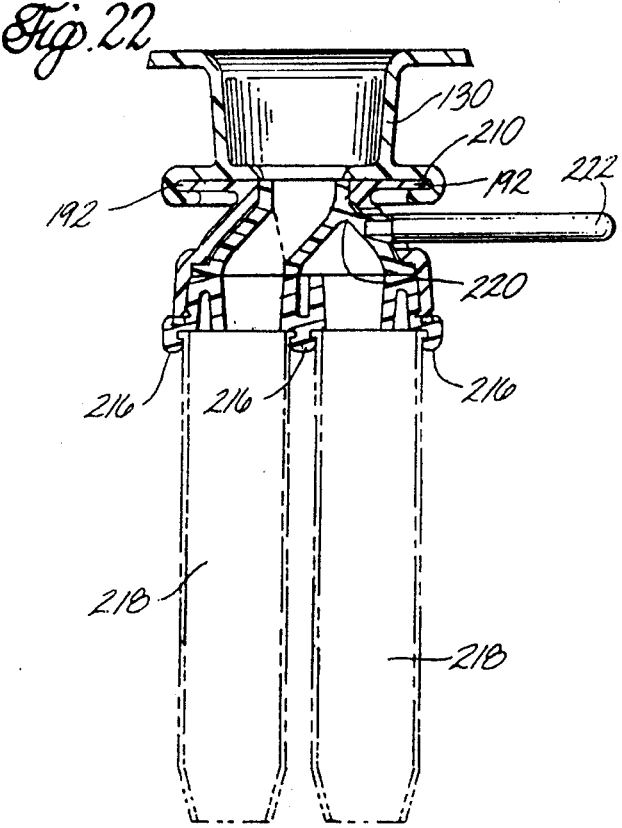
FIG. 22 is a front view of the adapter for cement dispensing cartridges of FIG. 21.

In another embodiment, an adapter is designed for use with cartridges which have flanges at the top of their tubular structure as shown in FIGS. 21 and 22. Adapters for use with such cartridges comprise a flange capture member 210 or slot which is the same as that described above. Generally commercially available cartridges which have a flanged top 192 are relatively small and in use it is desirable to have two such cartridges filled with cement at the same time. Therefore, it is desirable that the cartridge adapter have places for two cartridges.

In this embodiment of the present invention, the adapter handle 214 is attached to a holder which comprises two slots 216 on its lower side, adjacent to each other, into which are slid the flanges 212 of the cartridges 218. At a top side of the adapter are flanges for attaching to the bottom of the mixer, as described above. The adapter preferably comprises a means for diverting the cement, as it flows from the mixer, to each of the cartridges. The adapter comprises a lever 220 attached to a handle 222. When one cartridge is being filled the lever is in a first position which allows the cement to flow into a first cartridge. When the first cartridge is full the handle is moved so that the lever allows the cement to flow into a second cartridge.

In another embodiment the adapter of FIGS. 20 and 21 may include an "angled" top brace so that, when installed on the mixer, the adapter is angled away from the perpendicular plane to allow for clearance of large adapters and to allow easy fitting and removal of the adapters.

In operation, the housing 12 is sterilized by autoclaving and then connected to house vacuum line in the operating room. A presterilized bone cement kit is opened and liner 30 is placed in the mixer housing 12 and an injector gun or adapters (not shown) are placed on the cement outlet of the liner. Components of the cement, such as the powder which includes the methylmethacrylate monomer are then placed in the liner and vials containing catalyst, for the hardening of the cement, are placed in vial cavities 32 located in the liner. A programmed specifying the desired mixing and holding times, sequence of vacuum pump and mixer operation or other desired parameters are input via the key pad. Lid 14 of the housing is then closed to seal the components of the cement within the mixer.

Closing the lid breaks the vials, releases the catalyst into the other cement components and initiates the preprogrammed functions. A vacuum is applied to the interior of the liner to prevent the formation of air bubbles in the cement as it is mixed and also to remove fumes generated from the components of the cement. After the bone cement mixer has been evacuated the mixer is started.

At the end of the preselected mixing time, the mixer stops automatically and, in one embodiment of the present invention, sounds an alarm to alert the operator. A vacuum is again applied to the chamber to evacuate fumes which have built up during the mixing procedure. When the mixing is completed, the vacuum is released and pressure is applied to the chamber to evacuate the cement from the mixer by pushing the cement through a port located at the bottom of the mixer into a cement gun or various cartridges for dispensing the cement.

In a preferred embodiment of the present invention, the liner, alone or along with the cartridge adapter, are supplied in pre-sterilized packets. Therefore, the packets only need to be aseptically opened and the liners placed in the mixer chamber, for the bone cement mixer to be ready for use. Such procedures can easily be performed by a "sterile" person and an additional "non-sterile" person is not required for the routine operation of the mixer, after the mixer has been "setup." A "non-sterile" person is need initially to set-up the mixer by connecting it to the house vacuum line.

At the end of the mixing procedure the cartridge adapter packet is opened and a sterile cartridge is placed in the adapter, which is then attached to the mixer. The cement then flows into the cartridge without any intervention by the operator. Again this procedure is easily performed by a "sterile" person without the assistance of a "non-sterile" or an additional "sterile" person after the mixer has been initially "set-up." Therefore, the operation of the mixer is easily carried out by a single person, reducing the need for additional staff in the cement mixing procedure.

The above descriptions of exemplary embodiments of a mixing apparatus are for illustrative purposes. Variations will be apparent to those skilled in the art. For example, an injection gun designed specifically for use with the bone cement mixer could be used in place of the cartridge adapters described. Therefore, the present invention is not intended to be limited to the particular embodiments described above. The present invention may also be practiced in the absence of any element not specifically disclosed. The scope of the invention is defined by the following claims.

What is claimed is:

1. A method for preparing bone cement comprising:

placing dry components of the bone cement in a mixer;

placing vials containing catalyst for the bone cement in vial cavities within the mixer;

sealing the components of the cement within the mixer;

breaking the vials to release the catalyst into the dry components of the bone cement;

starting a preprogrammed mixing sequence; and collecting mixed cement.

2. A method for preparing bone cement as recited in claim 1, wherein the preprogrammed mixing sequence comprise:

applying a vacuum to the interior of the mixer;

starting a motor to drive an impeller within the mixer;

mixing for a preselected time period;

applying a vacuum to evacuate fumes from the interior of the mixer; and applying pressure to the interior of the mixer to discharge the mixed cement from the interior of the mixer.

3. An adapter for attaching different sized cartridges to a bone cement mixer comprising:
- an upper bracket comprising a tube with a stepped outer surface, wherein the steps result in different outer diameters,;
- a handle attached at its upper end to the upper bracket wherein the handle has a "U"-shaped projection attached to a lower end; and
- a lower bracket comprising:
  - a tube with a stepped inner surface, wherein the steps result in different inner diameters; and
  - a "U"-shaped bracket attached to the outer surface of the tube, wherein the "U"-shaped bracket is slidably mounted onto the "U"-shaped projection of the handle.

4. An adapter as recited in claim 3 further comprising a flange attached to the top of the upper bracket for attaching the adapter to a mixer chamber.

5. An adapter for attaching cartridges to a bone cement mixer comprising:
- an upper bracket comprising at least one flange capture member for slidably connecting a cement dispensing cartridge to the adapter; and
- a handle attached at its upper end to the upper bracket.

6. An adapter as recited in claim 5 further comprising a flange attached to the top of the upper bracket for attaching the adapter to a mixer chamber.

* * * * *